(12) United States Patent
Diner et al.

(10) Patent No.: US 8,216,809 B2
(45) Date of Patent: Jul. 10, 2012

(54) ORGANIC SOLVENT PRETREATMENT OF BIOMASS TO ENHANCE ENZYMATIC SACCHARIFICATION

(75) Inventors: Bruce A. Diner, Chadds Ford, PA (US); Paul Joseph Fagan, Wilmington, DE (US); Janine Fan, Hockessin, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 457 days.

(21) Appl. No.: 12/639,050

(22) Filed: Dec. 16, 2009

(65) Prior Publication Data
US 2010/0159519 A1    Jun. 24, 2010

Related U.S. Application Data

(60) Provisional application No. 61/139,170, filed on Dec. 19, 2008.

(51) Int. Cl.
*C12P 19/00* (2006.01)
*C12P 7/40* (2006.01)
*C12P 7/02* (2006.01)
*C12P 13/04* (2006.01)
*C12P 7/06* (2006.01)
*C12P 7/08* (2006.01)
*C07H 1/08* (2006.01)

(52) U.S. Cl. .......... 435/72; 435/106; 435/136; 435/151; 435/161; 435/163; 536/128

(58) Field of Classification Search .................. 435/72, 435/106, 136, 155, 161, 163; 536/128
See application file for complete search history.

(56) References Cited

U.S. PATENT DOCUMENTS

| | | | |
|---|---|---|---|
| 3,490,993 A | 1/1970 | Fisher et al. |
| 3,567,572 A | 3/1971 | Clayton et al. |
| 3,664,919 A | 5/1972 | Clayton et al. |
| 4,130,457 A | 12/1978 | Barker |
| 4,329,200 A | 5/1982 | Sarkanen |
| 4,451,567 A | 5/1984 | Ishibashi et al. |
| 4,597,830 A | 7/1986 | April et al. |
| 5,074,960 A | 12/1991 | Nimz et al. |
| 5,188,708 A | 2/1993 | Griggs et al. |
| 5,281,434 A | 1/1994 | Winowiski et al. |
| 5,630,906 A | 5/1997 | Boe et al. |
| 6,143,130 A | 11/2000 | Stigsson et al. |
| 2008/0299628 A1 | 12/2008 | Hallberg et al. |

FOREIGN PATENT DOCUMENTS

| | | |
|---|---|---|
| GB | 925524 A | 5/1963 |
| JP | 56116701 A | 9/1981 |
| RU | 2151228 C1 | 6/2000 |
| WO | 9736040 A1 | 10/1997 |

OTHER PUBLICATIONS

Avgerinos, G. C. et al., Selective Solvent Delignification for Fermentation Enhancement, Biotechnology and Bioengineering, 1983, pp. 67-83, vol. 25, No. 1 (Abstract attached).
Ahmed, A. et al., Steps for very-high yield pretreatment of aspen chips with alcohol, Journal of Pulp and Papers Science, Jan. 1994, pp. J9-J13, vol. 20, No. 1 (Abstract attached).
Nada, A. M. A. et al., Modified Kraft Pulping and Bagasse, Journal of Scientific Industrial Research, 1988, pp. 324-329, vol. 57, No. 6 (Abstract attached).
Selvam, Pannir et al., Catalytic solvent delignification of agricultural residues: Inorganic catalysts, Process Biochemistry, 1983, pp. 13-15, vol. 18, No. 3 (Abstract attached).
Usta, M. et al., ASAE pulping of wheat straw (Triticum aestivum L.), Cellulose Chemistry and Technology, Jan. 1999, pp. 91-102, vol. 33, No. 1 (Abstract attached).
Green, Jesse et al., Alkaline Pulping in Aqueous Alcohols and Amines, Tappi, May 1982, pp. 133-137, vol. 65, No. 5 (Abstract attached).
Schulek, E. et al., Formation and decomposition of sulfides, polysulfides, sulfites, and thiosulfates, Acta Chimica Academiae Scientiarum Hungaricae, 1953, pp. 125-138, vol. 3 (Abstract attached).
Ben-Ghedalia, Daniel et al., The Effect of Combined Chemical and Enzyme Treatments on the Saccharification and in vitro Digestion Rate of Wheat Straw, Biotechnology and Bioengineering, 1981, pp. 823-831, vol. 23, John Wiley & Sons, inc.
Ben-Ghedalia, Ben et al., Chemical treatments for increasing the digestibility of cotton straw, J. Agric. Sci., 1983, pp. 393-300, vol. 100.
Bijan, Leila, et al., Integrated ozone end biotreatment of pulp mill effluent and changes in biodegradability and molecular weight distribution of organic compounds, Water Research, 2005, pp. 3763-3772, vol. 39, Elsevier Ltd.
Brolin, A. et al., On the selectivity of ozone delignification of softwood kraft pulps, Wood Science and Technology, 1993, pp. 115-129, vol. 27, Springer-Verlag.
Kleinert, Theodor N., Organosolv pulping with aqueous alcohol, Tappi, Aug. 1974, pp. 99-102, vol. 57, No. 8.
Lee, Yong-Hyun et al., Evaluation of Organosolv Processes for the Fractionation and Modification of Corn Stover for Bioconversion, Biotechnology and Bioengineering, 1987, pp. 572-581, vol. 29, John Wiley & Sons, Inc.
Neely, W. C., Factors Affecting the Pretreatment of Biomass With Gaseous Ozone, Biotechnology and Bioengineering, 1984, pp. 059-065, vol. 26, John Wiley & Sons, Inc.

(Continued)

*Primary Examiner* — Herbert J Lilling

(57) ABSTRACT

Biomass is pretreated using an organic solvent solution under alkaline conditions in the presence of elemental sulfur and optionally one or more alkylamine and/or one or more additional nucleophile to fragment and extract lignin. Pretreated biomass is further hydrolyzed with a saccharification enzyme consortium. Fermentable sugars released by saccharification may be utilized for the production of target chemicals by fermentation.

28 Claims, 1 Drawing Sheet

OTHER PUBLICATIONS

Osawa, Zenjiro et al., The Action of Gaseous Reagents on Cellulosic Materials, II. Pulping of Wood with Ozone, Tappi, Feb. 1963, pp. 84-89, vol. 46, No. 2.

Pan, G. Y. et al., Model Compound Studies on the Cleavage of Glycosidic Bonds by Ozone in Aqueous Solution, Res. Chem. Intermed., 1995, pp. 205-222, vol. 21, Nos. 3-5.

Park, Jung-Keug et al., Ammonia Catalyzed Organosolv Delignification of Poplar, Chem. Eng. Comm., 1988, pp. 187-205, vol. 65, Gordon and Breach Science Publishers S.A.

Peter, Siegfried et al., Degradation of Lignin with Monomethylamine, Chemical Engineering Technology, 1992, pp. 213-217, vol. 15.

Quesada, Joaquin et al., Ozonation of Lignin Rich Solid Fractions From Corn Stalks, Journal of Wood Chemistry and Technology, 1999, pp. 115-137, vol. 19(1&2), Marcel Dekker, Inc.

Quesada, Joaquin et al., Lignin Organosolvolysis from Autohydrolyzed Corn (Zea mays) Stalks: Ozonation of both Solvolytic Solid and Juice, Journal of Applied Polymer Science, 1998, pp. 1867-1876, vol. 68, John Wiley and Sons, Inc.

Reitberger, Torbjorn et al., Involvement of Oxygen-Derived Free Radicals in Chemical and Biochemical Degradation of Lignin, ACS Symposium Series, 2001, pp. 255-271, vol. 785, American Chemical Society.

Vidal, Pierre Francois et al., Ozonolysis of Lignin—Improvement of in vitro Digestibility of Poplar Sawdust, Biomass, 1988, pp. 1-17, vol. 16, Elsevier Applied Science Publishers Ltd.

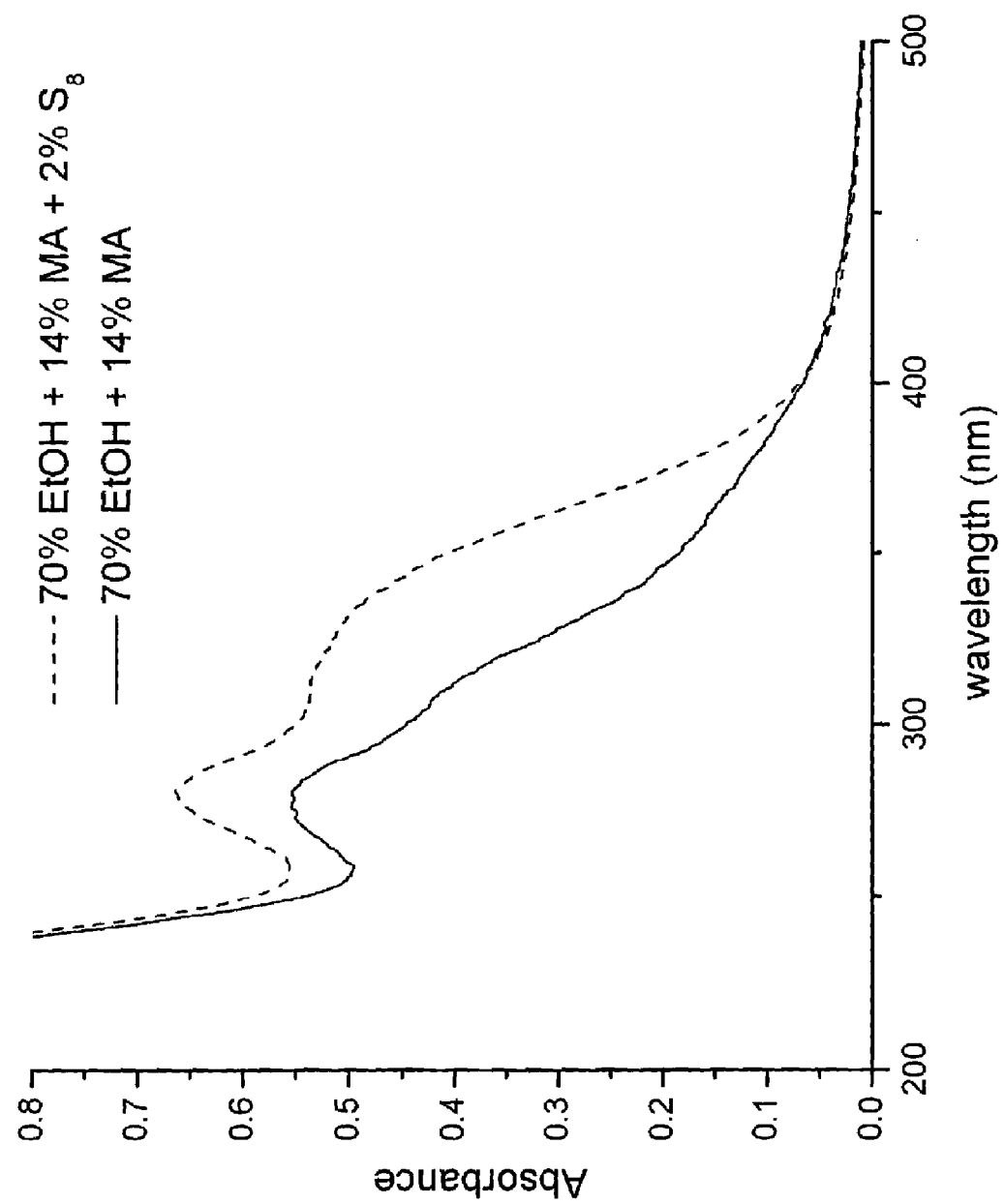

ORGANIC SOLVENT PRETREATMENT OF BIOMASS TO ENHANCE ENZYMATIC SACCHARIFICATION

The application claims the benefit of U.S. Provisional Application No. 61/139,170, filed Dec. 19, 2008, the disclosure of which is hereby incorporated in its entirety.

FIELD OF THE INVENTION

Methods for treating the carbohydrate-enriched lignocellulosic biomass to obtain fermentable sugars are provided and disclosed. Specifically, the biomass is first pretreated through simultaneous fragmentation and selective extraction of lignin in an organic solvent solution under alkaline conditions at elevated temperatures in the presence of elemental sulfur and various nucleophiles. The remaining carbohydrate-enriched solids in the pretreated biomass may then be subjected to enzymatic saccharification to obtain fermentable sugars, which may be subjected to further processing for the production of target products.

BACKGROUND OF THE INVENTION

Cellulosic and lignocellulosic feedstocks and wastes, such as agricultural residues, wood, forestry wastes, sludge from paper manufacture, and municipal and industrial solid wastes, provide a potentially large renewable feedstock for the production of chemicals, plastics, fuels and feeds. Cellulosic and lignocellulosic feedstocks and wastes, composed of cellulose, hemicellulose, pectins and of lignin are generally treated by a variety of chemical, mechanical and enzymatic means to release primarily hexose and pentose sugars, which can then be fermented to useful products.

Pretreatment methods are often used to make the polysaccharides of lignocellulosic biomass more readily accessible to cellulolytic enzymes. One of the major impediments to cellulolytic enzyme digest is the presence of lignin, a barrier that limits the access of the enzymes to their substrates, and a surface to which the enzymes bind non-productively. Because of the significant costs associated with enzymatic saccharification, it is desirable to minimize the enzyme loading by either inactivation of the lignin to enzyme adsorption or its outright extraction. Another challenge is the inaccessibility of the cellulose to enzymatic hydrolysis either because of its protection by hemicellulose and lignin or by its crystallinity. Pretreatment methods that attempt to overcome these challenges include: steam explosion, hot water, dilute acid, ammonia fiber explosion, alkaline hydrolysis (including ammonia recycled percolation), oxidative delignification and organosolv.

Organosolv methods, as previously practiced for the treatment of lignocellulose biomass, for either the production of pulp or for biofuels applications, while generally successful in lignin removal, have suffered from poor sugar recoveries, particularly of xylose. For example, the use of slightly acidic ethanol-water mixtures (e.g., EtOH 42 weight %) at elevated temperature to remove lignin from lignocellulosic biomass (Kleinert, T. N., Tappi, 57: 99-102, 1974) resulted in substantial loss of carbohydrate. Dilute acid hydrolysis at 95° C. followed by organic solvent extraction and enzymatic saccharification (Lee, Y-H., et al., Biotech. Bioeng., 29: 572-581, 1987) resulted in substantial loss of hemicellulose during hydrolysis, additional carbohydrate loss upon organic solvent extraction and poor yield (~50% of total carbohydrate) upon enzymatic saccharification of residue. Use of aqueous organic solvent containing ammonia at elevated temperatures to treat lignocellulosic biomass (Park J.-K. and Phillips, J. A., Chem. Eng. Comm., 65: 187-205, 1988) required the use of a high liquid to solids ratio in pretreatment and resulted in substantial loss of hemicellulose and poor enzymatic saccharification of cellulose. Treatment of biomass with gaseous water and methylamine followed by extraction with organic solvent and then extraction with water, required three steps and resulted in a substantial loss of carbohydrate (Siegfried, P. and Götz, R., Chem. Eng. Technol., 15: 213-217, 1992). Treatment with polyamines or ethylamine in water-aliphatic alcohol mixtures plus catalyst at elevated temperature required high liquid/solids ratio and low concentrations of alcohol led to poor sugar recovery, particularly of xylan (U.S. Pat. No. 4,597,830A). Thioglycolate in aqueous alkaline solution used to treat lignocellulosic biomass at elevated temperature, followed by a hot water wash required use of alkali-metal or alkaline-earth hydroxides. This method requires the costly disposal of inorganic ions, high weight % thioglycolate, and use of large volumes of water (U.S. Pat. No. 3,490,993). Treatment with organic solvent-water mixtures in the presence of sulfide/bisulfide at elevated temperatures required large solvent/solids ratio and resulted in substantial loss of carbohydrate, and elevated sulfur content (U.S. Pat. No. 4,329,200A).

Elemental sulfur has been used to generate polysulfides in the treatment of lignocellulosic biomass (e.g., U.S. Pat. Nos. 6,143,130, 3,664,919, 3,567,572 and 4,130,457). These entirely aqueous treatments improve pulp yields relative to the Kraft process and use polysulfides in place of sulfides to improve carbohydrate recovery. An impregnation step in which the biomass is incubated with polysulfide at moderate temperature is followed by an alkaline cook at elevated temperature. The disadvantages of these processes are that they require multiple steps, use large amounts of sulfur and high concentrations of caustic soda. They are intended for generation of pulp with low Kappa numbers. The cited patents give no quantitative indication of the recovery of hemicellulose or the suitability of the treated biomass for saccharification and fermentation.

Additional shortcomings of previously applied methods include, separate hexose and pentose streams (e.g., dilute acid), inadequate lignin extraction or lack of separation of extracted lignin from polysaccharide, particularly in those feedstocks with high lignin content (e.g., sugar cane bagasse, softwoods), need to dispose of waste products (e.g., salts formed upon neutralization of acid or base) and poor recoveries of carbohydrate due to breakdown or loss in wash steps. Other problems include the high cost of energy, capital equipment, and pretreatment catalyst recovery, and incompatibility with saccharification enzymes.

One of the major challenges of biomass pretreatment is to maximize the extraction or chemical neutralization (with respect to non-productive binding of cellulolytic enzymes) of the lignin while minimizing the loss of carbohydrate (cellulose plus hemicellulose) via low-cost, efficient processes, The higher the selectivity, the higher the overall yield of monomeric sugars following combined pretreatment and enzymatic saccharification.

There is therefore a need to develop a single step process using substantially lower concentrations of sulfur and recyclable base in the form of ammonia or alkylamines as opposed to the use of alkali metal hydroxides which are not amenable to either recycle or disposal. The current disclosure addresses this need. In this disclosure, an organic solvent-mediated fragmentation and selective extraction of lignin at elevated temperatures, under alkaline conditions, in combination of elemental sulfur and one or more alkylamine and optionally various nucleophiles is used. Surprisingly, this efficient and cost effective process resulted in significantly improved lignin fragmentation and extraction and high carbohydrate retention.

SUMMARY OF THE INVENTION

The present invention provides methods for producing readily saccharifiable carbohydrate-enriched biomass and for selectively extracting lignin from lignocellulosic biomass while nearly quantitatively retaining carbohydrate. The methods include treating lignocellulosic biomass with an organic solvent solution, such as EtOH in $H_2O$, under alkaline conditions at elevated temperatures, in the presence of elemental sulfur, and/or with one or more alkylamine to produce readily saccharifiable carbohydrate-enriched biomass. In certain embodiments the solvent solution further comprises additional nucleophilic components such as one or more alkylamine, ammonia, thiols and sulfides. Following pretreatment, the biomass may be further treated with a saccharification enzyme consortium to produce fermentable sugars. These sugars may be subjected to further processing for the production of target products.

Accordingly the invention provides a method for producing carbohydrate-enriched biomass comprising:
(a) providing lignocellulosic biomass comprising lignin;
(b) suspending the biomass of (a) in an organic solvent solution comprising water and elemental sulfur under alkaline conditions whereby a biomass-solvent suspension is formed;
(c) heating the biomass-solvent suspension to a temperature of about 100° C. to about 220° C. for about 5 minutes to about 5 hours whereby lignin is fragmented and is dissolved in the suspension; and
(d) filtering free liquid whereby the dissolved lignin is removed and whereby readily carbohydrate-enriched biomass is produced.

In another embodiment the invention provides a method of simultaneous fragmentation and selective extraction of lignin from lignocellulosic biomass comprising:
(a) providing:
  1) an amount of lignocellulosic biomass:
  2) elemental sulfur and a multi-component solvent solution comprising from about 40% to about 70% ethanol in water (v/v) and one or more alkylamine (s);
(b) contacting said biomass with the elemental sulfur and the multi-component solvent solution of (a) whereby a biomass-solvent mixture is formed;
(c) placing the mixture of (b) in a pressure vessel whereby the mixture is heated from about 100° C. to about 220° C. for about 5 minutes to about 5 hours whereby lignin is fragmented and dissolved in the solvent;
(d) removing the dissolved lignin of (c) by filtration; and
(e) washing the residual biomass with a organic solvent, whereby substantially lignin-free biomass is produced.

Particularly suitable alkylamines include those selected from the group consisting of $R-NH_2$, $R_2-NH$, $R_3N$, $(H_2N-R-NH_2)$, $(H_2N-R(NH_2)_2)$, $(HO-R-NH_2)$, $((HO)_2-R-NH_2)$, $(HO-R-(NH_2)_2)$, $(HS-R-NH_2)$, $((HS)_2-R-NH_2)$, $(HS-R-(NH_2)_2)$ and $(H_2N-R(OH)(SH))$ and combinations thereof, wherein R is independently a monovalent, divalent or trivalent 1-6 carbon alkane, alkene or alkyne, linear, cyclic or branched.

Particularly suitable feedstocks for use in the methods of the invention include but are not limited to switchgrass, waste paper, sludge from paper manufacture, corn fiber, corn cobs, corn husks, corn stover, grasses, wheat, wheat straw, hay, barley, barley straw, rice straw, sugar cane bagasse, sugar cane straw, yellow poplar, sorghum, soy, components obtained from processing of grains, trees, branches, roots, leaves, wood chips, sawdust, shrubs and bushes, vegetables, fruits, flowers, animal manure and combinations thereof.

BRIEF DESCRIPTION OF THE FIGURES

FIG. 1—FIG. 1 shows the UV absorbance spectra of the filtrate (diluted 1:5000 with 70% EtOH in $H_2O$ (v/v)) following pretreatment at 187° C. for 1 hour of 0.375 g of air-dried sugar cane bagasse (95.78% dry matter) with or without 2% elemental sulfur (w/w biomass) in 1.125 mL of 70% EtOH in $H_2O$ (v/v) plus 14% methylamine (w/w biomass).

DETAILED DESCRIPTION OF THE INVENTION

Applicants specifically incorporate the entire content of all cited references in this disclosure. Unless stated otherwise, all percentages, parts, ratios, etc., are by weight. Trademarks are shown in upper case. Further, when an amount, concentration, or other value or parameter is given as either a range, preferred range or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The present invention provides a process for the treatment of biomass in order to produce readily saccharifiable carbohydrate-enriched biomass to enhance the subsequent enzymatic saccharification step such that readily fermentable sugars can be obtained from saccharification.

A process involving a pretreatment step wherein lignin is simultaneously fragmented and extracted using an organic solvent under alkaline conditions at elevated temperatures in the presence of elemental sulfur and one or more alkylamine is employed. Additional nucleophiles may also be employed for further benefit. The treated biomass is then filtered and washed to remove solubilized lignin, acetic acid, acetamides, alkylamides and excess reagent and then digested with a saccharification enzyme consortium to produce readily fermentable sugars. The sugars may then be further processed to one or more target product. The removed lignin may also be further processed and utilized for other purposes (such as burning for energy) to increase efficiency.

Definitions

The following definitions are used in this disclosure:

"Room temperature" and "ambient" when used in reference to temperature refer to any temperature from about 15° C. to about 25° C.

"Fermentable sugars" refers to a sugar content primarily comprising monosaccharides and some disaccharides (that can be used as a carbon source by a microorganism (some polysaccharides may be present)) in a fermentation process to produce a target product. "Readily fermentable sugars" means that additional costly processing is not necessary and/ or that a fermentative microorganism can be contacted with the resulting sugars with minimal impediments from inhibitors or other components that may adversely affect fermentation.

"Lignocellulosic" refers to material comprising both lignin and cellulose. Lignocellulosic material may also comprise hemicellulose. In the processes described herein, lignin is dissolved and substantially removed from the lignocellulosic biomass to produce a carbohydrate-enriched biomass.

"Dissolved lignin" as referred to herein means the lignin that is dissolved in an organic solvent solution.

"II lignin" refers to acid-insoluble lignin.

"Autohydrolysis" refers to the hydrolysis of biomass in the presence of solvent (water or organic solvent plus water) plus heat with no further additions, such as without exogenous acid or base or hydrolytic enzyme addition.

"Cellulosic" refers to a composition comprising cellulose.

"Target product" refers to a chemical, fuel, or chemical building block produced by fermentation. Product is used in a broad sense and includes molecules such as proteins, including, for example, peptides, enzymes and antibodies. Also contemplated within the definition of target product are ethanol and butanol.

"Dry weight of biomass" refers to the weight of the biomass having all or essentially all water removed. Dry weight is typically measured according to American Society for Testing and Materials (ASTM) Standard E1756-01 (Standard Test Method for Determination of Total Solids in Biomass) or Technical Association of the Pulp and Paper Industry, Inc. (TAPPI) Standard T-412 om-02 (Moisture in Pulp, Paper and Paperboard).

"Selective extraction" means removal of lignin while substantially retaining carbohydrates.

"Solvent solution" and "an organic solvent solution", as used herein, is an organic solvent mixture in water that includes any organic liquid that dissolves a solid, liquid, or gaseous solute, resulting in a solution. The most suitable solvent solutions for this invention are organic solvents such as ethanol, methanol, n-propanol, isopropanol, n-butanol, 2-butanol, isobutanol, t-butanol, pentanol and hexanol and diols with the same number of carbons. They can also include aprotic solvents. The solvent solutions can include additional components in mixture with the solution, e.g., the solvent solution may include one or more nucleophile.

"Biomass" and "lignocellulosic biomass" as used herein refer to any lignocellulosic material, including cellulosic and hemi-cellulosic material, for example, bioenergy crops, agricultural residues, municipal solid waste, industrial solid waste, yard waste, wood, forestry waste and combinations thereof, and as further described below. Biomass has a carbohydrate content that comprises polysaccharides and oligosaccharides and may also comprise additional components, such as protein and/or lipid.

"Highly conserved" as used herein refers to the carbohydrate content of the lignocellulosic material after the processing steps described herein. In an embodiment of the invention, the highly conserved carbohydrate content provides for sugar yields after saccharification that are substantially similar to theoretical yields with minimal loss of sugar yield from the processes described herein. In an embodiment of the invention, highly-conserved with reference to carbohydrate content refers to the conservation of greater than or equal to 85% of the biomass carbohydrate as compared to biomass prior to pretreating as described herein.

"Preprocessing" as used herein refers to processing of lignocellulosic biomass prior to pretreatment. Preprocessing is any treatment of biomass that prepares the biomass for pretreatment, such as mechanically milling and/or drying to the appropriate moisture contact.

"Biomass-solvent suspension" refers to a mixture of biomass and solvent. The biomass-solvent solution may comprise additional components such as alkylamines, thioglycolate, ammonia, sulfides, etc.

"Saccharification" refers to the production of fermentable sugars from primarily polysaccharides by the action of hydrolytic enzymes. Production of fermentable sugars from pretreated biomass occurs by enzymatic saccharification by the action of cellulolytic and hemicellulolytic enzymes.

"Pretreating biomass" or "biomass pretreatment" as used herein refers to subjecting native or preprocessed biomass to chemical or physical action, or any combination thereof, rendering the biomass more susceptible to enzymatic saccharification or other means of hydrolysis prior to saccharification. For example, the methods claimed herein may be referred to as pretreatment processes that contribute to rendering biomass more accessible to hydrolytic enzymes for saccharification.

"Pretreatment filtrate" means the free liquid that is in contact with the biomass following pretreatment and which is separated by filtration.

"Pretreated Biomass" as used herein refers to native or preprocessed biomass that has been subjected to chemical or physical actions, rendering the biomass more susceptible to enzymatic saccharification or other means of hydrolysis prior to saccharification.

"Air-drying the filtered biomass" can be performed by allowing the biomass to dry through equilibration with the air of the ambient atmosphere.

"Readily saccharifiable biomass" means biomass that is carbohydrate-enriched and made more amenable to hydrolysis by cellulolytic or hemi-cellulolytic enzymes for producing monomeric and oligomeric sugars, i.e., pretreated biomass as described herein.

"Carbohydrate-enriched" as used herein refers to the biomass produced by the process treatments described herein. In one embodiment the readily saccharifiable carbohydrate-enriched biomass produced by the processes described herein has a carbohydrate concentration of greater than or equal to 85% of the dried biomass by weight, while having removed 75% or greater of the starting biomass lignin content based on dry weight.

"Heating the biomass suspension" means subjecting the biomass suspended in a solvent to a temperature greater than ambient or room temperature. Temperatures relevant to the present pretreatments are from about 100 to about 220° C., or from about 140 to about 180° C., or any temperature within or approximately these ranges.

"Filtering free liquid under pressure" means removal of unbound liquid through filtration, with some pressure difference on opposite faces of the filter.

"Alkaline" or "under alkaline conditions" means a pH of greater than 7.0. In the present invention, "under alkaline conditions", also means a pH of the biomass-solvent suspension equal to or greater than the pKas of the nucleophiles present such that these are substantially deprotonated and more highly reactive than in their protonated states. These nucleophiles would include alkylamines, and ammonia, thiols, polysulfides and hydrosulfide (if present).

"Divalent alkane" means a linear, branched or cyclic alkane with two open valences.

"Alkylamine" means an alkane containing an —$NH_2$ group in place of one H atom; e.g., ethylamine, isopropylamine, ethylhexylamine, cyclohexylamine, and as further defined below.

"Air-dried sample" means a pretreated sample which has been allowed to air-dry at ambient temperature and pressure to the point where its moisture content is in equilibrium with that of the ambient air, typically ≧85% dry matter.

"Substantially lignin-free biomass" means a pretreated sample in which about ≧75% of the lignin is removed.

"Dry biomass" means biomass with a dry matter content of ≧85%. Methods for drying the biomass include exposure at ambient temperature to vacuum or flowing air at atmospheric pressure and or heating in an oven or a vacuum oven.

"Multi-component solvent" means a solvent containing organic solvent, water, and reagents capable of chemical attack on the lignin.

"Pressure vessel" is a sealed vessel that may be equipped or not with a mechanism for agitation of a biomass/solvent suspension, in which a positive pressure is developed upon heating the lignocellulosic biomass.

"Nucleophile" is a chemical reagent capable of forming a covalent bond with its reaction partner by contributing both of the bonding electrons.

"Hydrolysate" refers to the liquid in contact with the lignocellulose biomass which contains the products of hydrolytic reactions acting upon the biomass (either enzymatic or not), in this case monomeric and oligomeric sugars.

"Organosolv" means a mixture of organic solvent and water which is typically in contact with biomass and in which the lignin or its fragments are soluble.

"Enzyme consortium" or "saccharification enzyme consortium" is a collection of enzymes, usually secreted by a microorganism, which in the present case will typically contain one or more cellulases, xylanases, glycosidases, ligninases and esterases.

"Monomeric sugars" or "simple sugars" consist of a single pentose or hexose unit, e.g., glucose, xylose and arabinose.

"Delignification" is the act of removing lignin from lignocellulosic biomass. In the context of this application, delignification means fragmentation and extraction of lignin from the lignocellulosic biomass using an organic solvent under alkaline conditions at elevated temperatures in the presence of alkylamines and optionally various nucleophiles.

"Fragmentation" is a process in which lignocellulosic biomass is treated with organic solvent under alkaline conditions breaking the lignin down into smaller subunits.

"Selective extraction" is a process by which fragmented lignin is dissolved by treatment with an organic solvent under alkaline conditions leaving behind the polysaccharide.

"Simultaneous fragmentation and selective extraction" as used herein refers to a fragmentation reaction performed in organic solvent such that the lignin fragments go into solution as soon as they are released from the bulk biomass.

Methods for pretreating lignocellulosic biomass to produce readily saccharifiable biomass are provided. These methods provide economical processes for rendering components of the lignocellulosic biomass more accessible or more amenable to enzymatic saccharification. The pretreatment is primarily chemical. In this disclosure the pretreatment is performed in the presence of nucleophiles, specifically in the presence of elemental sulfur and an alkylamine under alkaline conditions. Additional nucleophiles may also be present, such as $NH_3$, thiol, sulfide reagents, or combinations thereof. The presence of an organic solvent and alkaline conditions promotes lignin fragmentation and removal and carbohydrate retention.

In addition, the methods described in the present disclosure minimize the loss of carbohydrate during the pretreatment process and maximize the yield of solubilized (monomeric+oligomeric) sugars in saccharification.

As disclosed above the methods described herein include pretreating lignocellulosic material, with a solvent solution comprising the components described below, to produce a readily saccharifiable carbohydrate-enriched biomass.

Elemental Sulfur

According to the present method, elemental sulfur is added to the pretreatment in an organic solvent mixture, under alkaline conditions, prior to saccharification. Addition of elemental sulfur to the alkaline organic solvent mixture in the presence of alkylamines results in solubilization and disproportionation of the sulfur to produce polysulfide, hydropolysulfide, sulfide and hydrosulfide. These soft nucleophiles fragment the lignin, facilitating its extraction, and thereby increasing the accessibility of the carbohydrate-enriched biomass to enzymatic saccharification.

In accordance with the present methods it was unexpectedly discovered that elemental sulfur addition to the organic solvent solution under alkaline conditions resulted in increased lignin fragmentation and extraction, and accordingly, increased accessibility of the readily saccharifiable biomass to enzymatic saccharification. Specifically, in combination with one or more alkylamine, the presence of the elemental sulfur yielded a surprising effective amount of fermentable sugars following enzymatic saccharification.

In the present invention, concentrations of the elemental sulfur from 0.05% to 5% (w/w biomass) could be used. More specifically concentrations of 0.5 to 2% (w/w biomass) are more useful. Even more specifically concentrations of ~1% (w/w biomass) would be most useful for the present invention.

For the purpose of this invention, elemental sulfur undergoes disproportionation in the presence of the alkaline organic solvent solution to produce initially polysulfide (hydropolysulfide) and sulfite and later, sulfide (hydrosulfide) and thiosulfate. The polysulfide and sulfide are good soft nucleophiles. In this disclosure the pretreatment is performed in the presence of nucleophiles, e.g., alkylamines and the products of disproportionation of elemental sulfur. The presence of organic solvent and alkaline conditions assist lignin fragmentation. In addition, the methods described in the present disclosure minimize the loss of sugar during the pretreatment process and maximize the yield of solubilized (oligomer and monomeric) sugars in saccharification.

Solvents

The methods described herein include use of an organic solvent for pretreating biomass and specifically for fragmentation and extraction of lignin. Solvents useful in the present methods are frequently referred to in the art as Organosolv (E. Muurinen (2000) Organosolv Pulping, A review and distillation study related to peroxyacid pulping, Thesis, University of Oulu, pp. 314; S. Aziz, K. Sarkanen, Tappi J., 72/73: 169-175, 1989; A. K. Varsheny and D. Patel, J. Sci. Ind. Res., 47: 315-319, 1988; A. A. Shatalov and H. Pereira, BioResources 1:45-61, 2006; T. N. Kleinert, Tappi J., 57: 99-102, 1979). Practice of organosolv technology for biofuels, derived from Kleinert, which has advanced to the pilot scale using EtOH in $H_2O$ has been described (WO 20071051269; and X. Pan, N. Gilkes, J. Kadla, K. Pye, S. Saka, D. Gregg, K. Ehara, D. Xie, D. Lam, and J. Saddler, Biotechnol. Bioeng., 94: 851-861, 2006). While still at lab scale, use of acetone/$H_2O$ is described in U.S. Pat. No. 4,470,851. Further details on pretreatment technologies related to use of solvents and other pretreatments can be found in Wyman et al., (Bioresource Tech., 96: 1959, 2005); Wyman et al., (Bioresource Tech., 96: 2026, 2005); Hsu, ("Pretreatment of biomass" In Handbook on Bioethanol: Production and Utilization, Wyman, Taylor and Francis Eds., p. 179-212, 1996); and Mosier et al., (Bioresource Tech., 96: 673, 2005). Solvents are used herein for pretreating biomass to remove lignin. Delignification is typically conducted at temperatures of 165-225° C., at liquid to biomass ratios of 4:1 to 20:1, at liquid compositions of 50% organic solvent (v/v), and at reaction times between 0.5-12 h. A number of mono- and polyhydroxyalcohols have been tested as solvents. Ethanol, butanol and phenol have been used in these reactions (Park, J. K., and Phillips, J. A., Chem. Eng. Comm., 65: 187-205, 1988).

The organosolv or organic solvent solution pretreatment in the present methods may comprise a mixture of water and an organic solvent at selected condition parameters that include temperature, time, pressure, solvent-to-water ratio and solids-to-liquid ratio. The solvent can comprise, but is not limited to, alcohols and aprotic solvents (solvents that do not have a hydrogen atom bound to an oxygen as in a hydroxyl group or a nitrogen as in an amine group or a sulfur as in a thiol group, e.g., ketones). The alcohols may include methanol, ethanol, propanol, butanol, pentanol and hexanol and isomers thereof and diols with the same number of carbon atoms, such as 1,2-ethanediol, 1,2-propandiol, 1,3-propanediol, 1,3-hexanediol.

The concentration of the solvent in solution (i.e., water) in the present invention is from about 2 to about 90% (v/v), or from about 10% to about 85% or from about 20% to about 80% or from about 30% to about 80% or more preferably from about 40% to about 70% (v/v). Specifically, for purposes of an embodiment of the methods herein, EtOH in $H_2O$ mixtures from about 0%-80% (v/v) ethanol were examined and solutions containing 40-70% (v/v) EtOH were found to be most effective.

Additional Components of the Solvent Solution

In one embodiment, alkylamines are used for pretreatment of biomass according to the present methods as components of the solvent solution. Suitable alkylamines for this invention comprise: methylamine (MA), dimethylamine (DMA), trimethylamine (TMA), ethylamine, propylamine, and butylamine. The more suitable alkylamines for this invention include, but are not limited to MA and DMA. Alkylamines are strong bases owing to electron donation to the amine nitrogen by the alkyl chain carbons, and consist of primary amines (R—$NH_2$), secondary amines (R—N—R') and tertiary amines (R—N—(R')(R'')) where R, R' and R'' are alkyl chains. Specifically R could be selected from a group consisting of mono, di- and tri-amines, wherein R is independently a monovalent or divalent 1-6 carbon alkane, alkene or alkyne, linear, cyclic or branched. Examples of alkylamines include, mono, di- and tri-methylamine, mono, di- and tri-ethylamine, mono, di- and tri-propylamine, mono, di- and tri-butylamine. Alkylamines also include alkyl diamines ($H_2N$—R—$NH_2$), alcohol amines (HO—R—$NH_2$), thiolamines (HS—R—$NH_2$), and alcohol thiolamines ($H_2N$—R (OH)(SH)) where R is as defined. Suitable alkylamines for this invention comprise: MA, DMA, ethylamine, propylamine, and butylamine. The more suitable alkylamines for this invention include, but are not limited to MA and DMA. The concentration of the alkylamines according to present method may be used from about 1% to about 20 wt % of dry biomass. In accordance with the present methods alkylamines, especially MA and DMA, are highly active in a concentration range of from 10 to 14% relative to dry weight of biomass.

In another embodiment, ammonia may be employed as an additional component of the solvent solution in the presence of alkylamines, resulting in increasing lignin fragmentation and extraction, and resulting in an increased accessibility of the carbohydrate-enriched biomass to enzymatic saccharification. A further specific embodiment is the use of ammonia and MA in the solvent solution. One aspect includes use of elemental sulfur and ammonia in solvent solutions comprising MA as the alkylamine in the solvent solution. For example, a solvent solution comprising 20-80% v/v EtOH in $H_2O$ with 1% elemental sulfur, 2% to 16% $NH_3$ (w/w biomass) and MA.

Other inorganic bases could be used at various concentrations of at least from 0.5% to about 16% (wt % of dry biomass). More suitable are the concentrations from 1% to 10%. Most suitable are the concentrations between 2% to 8% (wt % of dry biomass).

Liqnocellulosic Biomass

The lignocellulosic biomass pretreated herein includes, but is not limited to, bioenergy crops, agricultural residues, municipal solid waste, industrial solid waste, sludge from paper manufacture, yard waste, wood and forestry waste. Examples of biomass include, but are not limited to corn cobs, crop residues such as corn husks, corn stover, grasses, wheat, wheat straw, barley, barley straw, hay, rice straw, switchgrass, waste paper, sugar cane bagasse, sugar cane straw, yellow poplar, sorghum, soy, components obtained from milling of grains, trees, branches, roots, leaves, wood chips, sawdust, shrubs and bushes, vegetables, fruits, flowers and animal manure.

In one embodiment, the lignocellulosic biomass includes agricultural residues such as corn stover, wheat straw, barley straw, oat straw, rice straw, canola straw, and soybean stover; grasses such as switchgrass, miscanthus, cord grass, and reed canary grass; fiber process residues such as corn fiber, beet pulp, pulp mill fines and rejects and sugar cane bagasse; sugar cane straw and sorghum; forestry wastes such as yellow poplar, aspen wood, other hardwoods, softwood and sawdust; and post-consumer waste paper products; as well as other crops or sufficiently abundant lignocellulosic material.

In another embodiment, biomass that is useful for the invention includes biomass that has a relatively high carbohydrate content, is relatively dense, and/or is relatively easy to collect, transport, store and/or handle.

In another embodiment of the invention, biomass that is useful includes corn cobs, corn stover, sugar cane bagasse, sugar cane straw, yellow poplar and switchgrass.

The lignocellulosic biomass may be derived from a single source, or biomass can comprise a mixture derived from more than one source; for example, biomass could comprise a mixture of corn cobs and corn stover, or a mixture of stems or stalks and leaves.

In the present method, the biomass dry weight is at an initial concentration of at least about 9% up to about 80% of the weight of the biomass-solvent suspension during pretreatment. More suitably, the dry weight of biomass is at a concentration of from about 15% to about 70%, 15% to about 60%, or about 15% to about 50% of the weight of the biomass-solvent suspension. The percent of biomass in the biomass-solvent suspension is kept high to reduce the total volume of pretreatment material, decreasing the amount of solvent and reagents required and making the process more economical.

The biomass may be used directly as obtained from the source, or may be subjected to some preprocessing, for example, energy may be applied to the biomass to reduce the size, increase the exposed surface area, and/or increase the accessibility of lignin and of cellulose, hemicellulose, and/or oligosaccharides present in the biomass to organosolv pretreatment and to saccharification enzymes used, respectively, in the second and third steps of the method. Energy means useful for reducing the size, increasing the exposed surface area, and/or increasing the accessibility of the lignin, and the cellulose, hemicellulose, and/or oligosaccharides present in the biomass to the organosolv pretreatment and to saccharification enzymes include, but are not limited to, milling, crushing, grinding, shredding, chopping, disc refining, ultrasound, and microwave. This application of energy may occur before or during pretreatment, before or during saccharification, or any combination thereof.

Drying prior to pretreatment may occur as well by conventional means, such as exposure at ambient temperature to vacuum or flowing air at atmospheric pressure and or heating in an oven at atmospheric pressure or a vacuum oven.

Pretreatment Conditions

Pretreatment of biomass with the organic solvent solution comprising elemental sulfur and ammonia and/or alkylamines, under alkaline conditions, is carried out in any suitable vessel. Typically the vessel is one that can withstand pressure, has a mechanism for heating, and has a mechanism for mixing the contents. Commercially available vessels include, for example, the Zipperclave® reactor (Autoclave Engineers, Erie, Pa.), the Jaygo reactor (Jaygo Manufacturing, Inc., Mahwah, N.J.), and a steam gun reactor (described in General Methods Autoclave Engineers, Erie, Pa.). Much larger scale reactors with similar capabilities may be used. Alternatively, the biomass and organosolv solution may be combined in one vessel, then transferred to another reactor. Also biomass may be pretreated in one vessel, then further processed in another reactor such as a steam gun reactor (described in General Methods; Autoclave Engineers, Erie, Pa.).

The pretreatment reaction may be performed in any suitable vessel, such as a batch reactor or a continuous reactor. One skilled in the art will recognize that at higher temperatures (above 100° C.), a pressure vessel is required. The suitable vessel may be equipped with a means, such as impellers, for agitating the biomass-organosolv mixture. Reactor design is discussed in Lin, K.-H., and Van Ness, H. C. (in Perry, R. H. and Chilton, C. H. (eds), Chemical Engineer's Handbook, $5^{th}$ Edition (1973) Chapter 4, McGraw-Hill, N.Y.). The pretreatment reaction may be carried out either as a batch or a continuous process.

Prior to contacting the biomass with solvent, vacuum may be applied to the vessel containing the biomass. By evacuating air from the pores of the biomass, better penetration of the solvent into the biomass may be achieved. The time period for applying vacuum and the amount of negative pressure that is applied to the biomass will depend on the type of biomass and can be determined empirically so as to achieve optimal pretreatment of the biomass (as measured by the production of fermentable sugars following saccharification).

The heating of the biomass with solvent is carried out at a temperature of from about 100° C. to about 220° C., about 150° C. to 200° C., or about 165° C. to about 195° C. The heated solution may be cooled rapidly to room temperature. In still another embodiment, the heating of the biomass is carried out at a temperature of about 180° C. Heating of the biomass-solvent suspension may occur for about 5 minutes to about 5 hours, or for about 30 minutes to about 3 hours, or more preferably from about 1 to 2 hours.

The pretreatment of biomass plus elemental sulfur with the solvent solution and one or more alkylamine occurs under alkaline conditions at a pH that is equal to or greater than the pKa of the nucleophiles present. Under these high pH conditions at least 50% of the nucleophiles are in their deprotonated states. Deprotonation typically increases the reactivity of the nucleophiles. The nucleophiles present, in addition to alkylamine and polysulfides (hydropolysulfides) and sulfides (hydrosulfides), can include ammonia and thiols.

For the pretreatment method described herein, the temperature, pH, time for pretreatment and concentration of reactants such as the organic solvent and the elemental sulfur and ammonia and/or an alkylamine, under alkaline conditions, and the concentration of one or more additional reagents, biomass concentration, biomass type and biomass particle size are related; thus these variables may be adjusted as necessary for each type of biomass to optimize the pretreatment processes described herein.

Following pretreatment at elevated temperature the biomass is filtered under pressure. The filtration may either be preceded or not by cooling. Following filtration, the biomass may be washed one or more times with hydrated organic solvent at elevated or at ambient temperature. It may then either be washed with water or dried to remove the organic solvent and then saccharified. Methods for drying the biomass were described above.

To assess performance of the pretreatment (i.e., the production of readily saccharifiable carbohydrate-enriched biomass and subsequent saccharification), separately or together, the theoretical yield of sugars derivable from the starting biomass can be determined and compared to measured yields. Pretreatment performance may be further assessed by relating how enzyme loadings affect target product yields in overall system performance.

Further Processing

Saccharification

Following pretreatment, the readily saccharifiable carbohydrate-rich biomass comprises a mixture of organic solvent, elemental sulfur, alkylamine, polysulfide, hydro polysulfide, sulfide, hydrosulfide and ammonia; fragmented and extracted lignin; and polysaccharides. Prior to further processing, elemental sulfur, alkylamine, polysulfide, sulfide and hydrosulfide and ammonia, and lignin fragments may be removed from the pretreated biomass by filtration and washing the sample with EtOH in $H_2O$ (0% to 100% EtOH v/v) or water. The biomass may then either be washed with water to remove EtOH or be dried resulting in carbohydrate-enriched, readily saccharifiable biomass and the concentration of glucan, xylan and acid-insoluble lignin content of the readily saccharifiable biomass may be determined using analytical means well known in the art. It is a real benefit of this invention that the pretreated biomass can be either washed with water or dried for saccharification. The readily saccharifiable biomass may then be further hydrolyzed in the presence of a saccharification enzyme consortium to release oligosaccharides and/or monosaccharides in a hydrolysate.

Surfactants such as Tween 20 or Tween 80 or polyoxyethylenes such as PEG 2000, 4000 or 8000 may be added to improve the saccharification process (U.S. Pat. No. 7,354,743 B2, incorporated herein by reference). The addition of surfactant (e.g., Tween 20) to the enzymatic saccharification often enhances the rate and yield of monomeric sugar release. It is likely that the surfactant coats any residual lignin, decreasing the non-productive binding of the enzyme to the lignin. An alternative approach is to either enhance the extraction of lignin in the pretreatment or to modify the lignin chemically such that less enzyme is lost to lignin adsorption.

Saccharification enzymes and methods for biomass treatment are reviewed in Lynd, L. R., et al., (Microbiol. Mol. Biol. Rev., 66: 506-577, 2002). The saccharification enzyme consortium may comprise one or more glycosidases; the glycosidases may be selected from the group consisting of cellulose-hydrolyzing glycosidases, hemicellulose-hydrolyzing glycosidases, and starch-hydrolyzing glycosidases. Other enzymes in the saccharification enzyme consortium may include peptidases, lipases, ligninases and sterases.

The saccharification enzyme consortium comprises one or more enzymes selected primarily, but not exclusively, from the group "glycosidases" which hydrolyze the ether linkages of di-, oligo-, and polysaccharides and are found in the enzyme classification EC 3.2.1.x (Enzyme Nomenclature 1992, Academic Press, San Diego, Calif. with Supplement 1 (1993), Supplement 2 (1994), Supplement 3 (1995, Supplement 4 (1997) and Supplement 5 [in Eur. J. Biochem., 223: 1-5, 1994; Eur. J. Biochem., 232:1-6, 1995; Eur. J. Biochem., 237:1-5, 1996; Eur. J. Biochem., 250:1-6, 1997; and Eur. J. Biochem., 264:610-650 1999, respectively]) of the general group "hydrolases" (EC 3.). Glycosidases useful in the present method can be categorized by the biomass component that they hydrolyze. Glycosidases useful for the present method include cellulose-hydrolyzing glycosidases (for example, cellulases, endoglucanases, exoglucanases, cellobiohydrolases, β-glucosidases), hemicellulose-hydrolyzing glycosidases (for example, xylanases, endoxylanases, exoxylanases, β-xylo-sidases, arabino-xylanases, mannases, galactases, pectinases, glucuro-nidases), and starch-hydrolyzing glycosidases (for example, amylases, α-amylases, β-amylases, glucoamylases, α-glucosidases, isoamylases). In addition, it may be useful to add other activities to the saccharification enzyme consortium such as peptidases (EC 3.4.x.y), lipases (EC 3.1.1.x and 3.1.4.x), ligninases (EC 1.11.1.x), and feruloyl esterases (EC 3.1.1.73) to help release polysaccharides from other components of the biomass. It is well known in the art that microorganisms that produce polysaccharide-hydrolyzing enzymes often exhibit an activity, such as cellulose degradation, that is catalyzed by several enzymes or a group of enzymes having different substrate specificities. Thus, a "cellulase" from a microorganism may comprise a group of enzymes, all of which may contribute to the cellulose-degrading activity. Commercial or non-commercial enzyme preparations, such as cellulase, may comprise numerous enzymes depending on the purification scheme utilized to obtain the enzyme. Thus, the saccharification enzyme consortium of the present method may comprise enzyme activity, such as "cellulase", however it is recognized that this activity may be catalyzed by more than one enzyme.

Saccharification enzymes may be obtained commercially, in isolated form, such as Spezyme® CP cellulase (Genencor International, Rochester, N.Y.) and Multifect® xylanase (Genencor). In addition, saccharification enzymes may be expressed in host microorganisms at the biofuels plant, including using recombinant microorganisms.

One skilled in the art would know how to determine the effective amount of enzymes to use in the consortium and adjust conditions for optimal enzyme activity. One skilled in the art would also know how to optimize the classes of enzyme activities required within the consortium to obtain optimal saccharification of a given pretreatment product under the selected conditions.

Preferably the saccharification reaction is performed at or near the temperature and pH optima for the saccharification enzymes. The temperature optimum used with the saccharification enzyme consortium in the present method ranges from about 15° C. to about 100° C. In another embodiment, the temperature optimum ranges from about 20° C. to about 80° C. and most typically 45-50° C. The pH optimum can range from about 2 to about 11. In another embodiment, the pH optimum used with the saccharification enzyme consortium in the present method ranges from about 4 to about 5.5.

The saccharification can be performed for a time of about several minutes to about 120 hours, and preferably from about several minutes to about 48 hours. The time for the reaction will depend on enzyme concentration and specific activity, as well as the substrate used its concentration (i.e., solids loading) and the environmental conditions, such as temperature and pH. One skilled in the art can readily determine optimal conditions of temperature, pH and time to be used with a particular substrate and saccharification enzyme(s) consortium.

The saccharification can be performed batch-wise or as a continuous process. The saccharification can also be performed in one step, or in a number of steps. For example, different enzymes required for saccharification may exhibit different pH or temperature optima. A primary treatment can be performed with enzyme(s) at one temperature and pH, followed by secondary or tertiary (or more) treatments with different enzyme(s) at different temperatures and/or pH. In addition, treatment with different enzymes in sequential steps may be at the same pH and/or temperature, or different pHs and temperatures, such as using cellulases stable and more active at higher pHs and temperatures followed by hemicellulases that are active at lower pHs and temperatures.

The degree of solubilization of sugars from biomass following saccharification can be monitored by measuring the release of monosaccharides and oligosaccharides. Methods to measure monosaccharides and oligosaccharides are well known in the art. For example, the concentration of reducing sugars can be determined using the 1,3-dinitrosalicylic (DNS) acid assay (Miller, G. L., Anal. Chem., 31: 426-428, 1959). Alternatively, sugars can be measured by HPLC using an appropriate column as described below.

Fermentation to Target Products

The readily saccharifiable biomass produced by the present methods may be hydrolyzed by enzymes as described above to produce fermentable sugars which then can be fermented into a target product. "Fermentation" refers to any fermentation process or any process comprising a fermentation step. Target products include, without limitation, alcohols (e.g., arabinitol, butanol, ethanol, glycerol, methanol, 1,3-propanediol, sorbitol, and xylitol); organic acids (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, propionic acid, succinic acid, and xylonic acid); ketones (e.g., acetone); amino acids (e.g., aspartic acid, glutamic acid, glycine, lysine, serine, and threonine); gases (e.g., methane, hydrogen ($H_2$), carbon dioxide ($CO_2$), and carbon monoxide (CO)).

Fermentation processes also include processes used in the consumable alcohol industry (e.g., beer and wine), dairy industry (e.g., fermented dairy products), leather industry, and tobacco industry.

Further to the above, the sugars produced from saccharifying the pretreated biomass as described herein may be used to produce in general, organic products, chemicals, fuels, commodity and specialty chemicals such as xylose, acetone, acetate, glycine, lysine, organic acids (e.g., lactic acid), 1,3-propanediol, butanediol, glycerol, 1,2-ethanediol, furfural, polyhydroxy-alkanoates, cis,cis-muconic acid, and animal feed (Lynd, L. R., Wyman, C. E., and Gerngross, T. U., Biocom. Eng. Biotechnol. Prog., 15: 777-793, 1999; and Philippidis, G. P., Cellulose bioconversion technology, in Handbook on Bioethanol: Production and Utilization, Wyman, C. E., ed., Taylor & Francis, Washington, D.C., 179-212, 1996; and Ryu, D. D. Y., and Mandels, M., Cellulases: biosynthesis and applications, Enz. Microb. Technol., 2: 91-102, 1980).

Potential coproduction of products may also be produced, such as multiple organic products from fermentable carbohydrate. Lignin-rich residues remaining after pretreatment and fermentation can be converted to lignin-derived chemicals, chemical building blocks or used for power production.

Conventional methods of fermentation and/or saccharification are known in the art including, but not limited to, saccharification, fermentation, separate hydrolysis and fermentation (SHF), simultaneous saccharification and fermentation (SSF), simultaneous saccharification and cofermentation (SSCF), hybrid hydrolysis and fermentation (HHF), and direct microbial conversion (DMC).

SHF uses separate process steps to first enzymatically hydrolyze cellulose to sugars such as glucose and xylose and then ferment the sugars to ethanol. In SSF, the enzymatic hydrolysis of cellulose and the fermentation of glucose to ethanol is combined in one step (Philippidis, G. P., supra). SSCF includes the cofermentation of multiple sugars (Sheehan, J., and Himmel, M., Biotechnol. Prog. 15: 817-827, 1999). HHF includes two separate steps carried out in the same reactor but at different temperatures, i.e., high temperature enzymatic saccharification followed by SSF at a lower temperature that the fermentation strain can tolerate. DMC combines all three processes (cellulase production, cellulose hydrolysis, and fermentation) in one step (Lynd, L. R., Weimer, P. J., van Zyl, W. H., and Pretorius, I. S., Microbiol. Mol. Biol. Rev., 66: 506-577, 2002).

These processes may be used to produce target products from the readily saccharifiable biomass produced by the pretreatment methods described herein.

Advantages of the Present Methods

The present invention uses organic solvent, under alkaline conditions, with elemental sulfur in the presence of one or more alkylamine to fragment biomass lignin in a single step. The fragmented lignin is highly soluble in this solvent solution. Disproportionation of elemental sulfur in the organic solvent, under alkaline conditions, generates polysulfides and sulfides, which are among the best soft nucleophiles, to perform substitution reactions on the aryl ethers of the lignin. Elemental sulfur disproportionates to produce polysulfide and sulfide in the presence of ammonia and/or alkylamines. Together these nucleophiles fragment the lignin which then dissolves in the organic solvent. Liginin extraction is typically ≧75% and recovery of carbohydrate is close to quantitative. The present process uses low concentrations of sulfur. It also uses low concentrations of base in the form of ammonia or alkylamines, which are recyclable, as opposed to the use of alkali metal hydroxides which are not amenable to recycle or disposal.

The alkaline conditions also favor the formation of quinone methides from lignin. These are also readily attacked by sulfides. The presence of ammonia and/or alkylamines, in addition to raising the pH, supplements the sulfide/polysulfide nucleophilic chemistry in attacking the lignin. Polysulfides as well as the ammonia and/or alkylamines likely protect the polysaccharide against peeling reactions, that result in monosaccharide release and loss at high pH. Polysulfides likely do so via the oxidation of the reducing end aldehyde to the corresponding carboxylic acid while ammonia and alkylamines likely do so via imine formation. The use of alkylamines and/or ammonia as bases avoids the generation of an inorganic waste stream which would otherwise add to the financial and environmental cost of the process. Sulfides can also act as reducing agents, promoting the reduction of quinone methides, eliminating β-aryl ethers as phenoxyl radicals. The generation of sulfides and polysulfides, by disproportionation of elemental sulfur, in the lignocellulosic biomass pretreatment process therefore enhances lignin fragmentation and suppresses carbohydrate loss, increasing the selectivity of lignin extraction with respect to carbohydrate, producing carbohydrate-enriched biomass that is highly susceptible to enzymatic saccharification. Methods described in this invention for pretreatment of the lignocellulosic biomass using an organic solvent-mediated fragmentation in the presence of elemental sulfur, alkylamines and various nucleophiles in combination with selective extraction of lignin at elevated temperatures under alkaline conditions will provide a cost-effective process to obtain carbohydrate-enriched biomass for enzymatic saccharification. Such biomass then, produces very high yields of fermentable sugars (glucose, as well as xylose) for their bioconversion to value-added chemicals and fuels.

EXAMPLES

Pretreatment of Biomass to Obtain Readily Saccharifiable Carbohydrate-Enriched Biomass The goal of the experimental work described below was to develop an economic pretreatment process for lignocellulose that maximized both lignin extraction and sugar retention and to produce a readily saccharifiable biomass that may be further processed to result in a maximal monomeric sugar yield following enzymatic saccharification. The approach adopted was to selectively fragment and extract the lignin into a suitable solvent while retaining the sugars in the solids residue. The following experiments show the development of a solvent solution that combines the presence of elemental sulfur and nucleophiles like one or more alkylamine, $NH_3$ and thiol for selective extraction of lignin. It was found that the combined organic solvent, under alkaline conditions, and in the presence of one or more alkylamine and optionally certain nucleophiles like $NH_3$ and thiol reactants selectively fragmented and dissolved the lignin components of biomass providing for the generation of readily saccharifiable carbohydrate-enriched biomass.

Switchgrass, corn cob, sugar cane straw, yellow poplar and sugar cane bagasse were milled in a Wiley knife mill through a 1 mm screen prior to pretreatment.

The following abbreviations are used in the Examples: "HPLC" is High Performance Liquid Chromatography, "C" is degrees Centigrade or Celsius; "%" is percent; "wt" is weight; "w/w" is weight for weight; "mL" is milliliter; "OD" is outer diameter; "ID" is internal diameter; "h" is hour(s); "rpm" is revolution per minute; "EtOH" is ethanol; "mg/g" is milligram per gram; "g/100 mL" is gram per 100 milliliters; "N" is normal; "g" is gram; "NaOH" is sodium hydroxide; "w/v" is weight per volume; "v/v" is volume for volume; "$NH_3$" is ammonia; "mm" is millimeter; "mL/min" is milliliter per minute; "min" is minutes; "mM" is millimolar.

Materials

Sulfuric acid, ammonium hydroxide, acetic acid, acetamide, yeast extract, 2-morpholinoethanesulfonic acid (MES), potassium phosphate, glucose, xylose, tryptone, sodium chloride, citric acid, monomethyl and dimethylamine were obtained from Sigma-Aldrich (St. Louis, Mo.). Spezyme CP and Multifect CX12L were from Genecor (Genencor International, Palo Alto, Calif.) and Novozyme 188 was from Novozyme (Bagsvaerd, Denmark).

Example 1

Effective Ethanol Concentration

The purpose of this Example was to examine the effect of the concentration of solvent (e.g., ethanol) in water on the recovery of carbohydrate and on the solubilization/extraction of lignin in the absence of pH control. Bagasse (0.2 g, 95.78% dry matter) was suspended in 1.56 mL of an EtOH in water solution containing various concentrations (from 0 to 80%) of EtOH. The suspensions were loaded into type 316 stainless steel tubing (¼ inches ID, ⅜ inches OD, 4 inches long) capped by Swagelock fittings (Penn Fluid System Technologies, Huntingdon Valley, Pa.). These were placed in a fluidized sand bath (Techne Model SBS-4, Techne Inc., Burlington, N.J.) and heated at 180° C. for 2 h and cooled rapidly by plunging into a water bath at room temperature. The samples were removed from the tubes and filtered by centrifugation at 14,000 rpm using Spin-X filters (Costar, Corning Inc., Corning N.Y.) at room temperature in a table top centrifuge (Spectrifuge 16M, Labnet International Inc., Edison, N.J.) to remove the dissolved lignin. The retentate of each sample was washed (4×) with 0.5 mL of EtOH in $H_2O$ using the same EtOH concentration as used in the 180° C. treatment (0-80% EtOH in $H_2O$). The samples were then allowed to air dry at room temperature (to ~92% dry matter) and the glucan, xylan and acid-insoluble lignin contents of the residues determined using the National Renewable Energy Laboratory (NREL) procedure (Determination of Structural Carbohydrates and Lignin in Biomass—Version 2006, Amie Sluiter et al., available from the NREL website.

Subsequent Enzymatic Saccharification

The air-dried sample prepared above was suspended in 50 mM citrate buffer, pH 4.6 at a ~14% solids loading. The saccharification enzymes, e.g. Spezyme CP, Multifect CX12L and Novozyme 188 were added at concentrations of 6:3:6 mg/g cellulose, respectively. Also added were 1% (w/v) Tween 20 and 0.01% (w/v) $NaN_3$, the latter to prevent microbial growth. Samples (~0.4 mL) were placed in screw cap vials containing two 5 mm glass beads and incubated at 46° C. on a rotary shaker run at 250 rpm. Aliquots were removed for analysis at 4 h and at every 24 h interval from the start and diluted 41.25-fold with 0.01 N $H_2SO_4$. The samples were then filtered through Spin-X filters and the filtrates were analyzed by HPLC (Agilent series 1100/1200, Agilent Technologies, Wilmington, Del.). A BioRad HPX-87H Aminex column (Bio-Rad Laboratories, Hercules Calif. 94547 was used to fractionate the released sugars using 0.01 N $H_2SO_4$ as the mobile phase at a flow rate of 0.6 mL/min. The column was maintained at 60° C. A differential refractive index detector was used to detect the eluted sugars and was maintained at 55° C. The retention times for glucose, xylose and arabinose were 9.05, 9.72 and 10.63 min, respectively). Table 1A outlines the percentages of glucan and xylan recovery and the percent change in acid insoluble (II) lignin content after pretreatments at EtOH concentrations of 0%-80%.

TABLE 1A

Glucan and xylan recovery following pretreatment according to Example 1

| Pretreatment (% EtOH in water) | % Glucan recovery in residue | % Xylan recovery in residue | AI lignin content % change |
|---|---|---|---|
| 0 | 83.0% | 29.0% | +27.6% |
| 20 | 88.7% | 30.8% | +15.2% |
| 40 | 86.0% | 57.6% | −10% |
| 60 | 91.9% | 87.4% | −25.6% |
| 80 | 88.6% | 91.1% | −28.8% |

Results shown in Table 1A indicate that lignin extraction increased with increasing EtOH content presumably because the solubility of lignin increased with increasing EtOH concentration. However, the amount of lignin extracted remained modest even at high ethanol concentrations.

Hemicellulose hydrolysis and the solubility of xylose oligomers decreases with increasing EtOH, increasing the recovery of xylan and xylose oligomers in the residue. The amount of acetate liberated by the pretreatment also decreased with increasing EtOH content, consistent with decreasing auto hydrolysis of the biomass at increasing EtOH concentration.

Table 1B shows the glucose and xylose yields after 96 h of enzymatic saccharification following pretreatment at different EtOH concentrations. The saccharification of cellulose increased when the concentration of EtOH in pretreatment was increased from 0 to 20%, but then declined with higher pretreatment concentrations of EtOH. A likely decrease in partial hydrolysis of lignin and cellulose (increase in degree of polymerization, of cellulose which lowered the glucose yield on subsequent saccharification-Table 1B) was observed at concentrations of more than 20% EtOH.

TABLE 1B

Monomeric glucose and xylose yields following enzymatic saccharification for 96 h, pretreated as described in Example 1

| % EtOH in water (v/v) | Glucose monomer saccharification only (% theoretical yield) | Xylose monomer saccharification only (% theoretical yield) | Glucose monomer overall yield (% theoretical yield) | Xylose monomer overall yield (% theoretical yield) |
|---|---|---|---|---|
| 0 | 38.43 | 34.98 | 31.86 | 10.16 |
| 20 | 44.48 | 45.52 | 39.46 | 14.01 |
| 40 | 29.62 | 38.55 | 25.45 | 22.23 |
| 60 | 16.81 | 24.64 | 15.45 | 21.52 |
| 80 | 6.8 | 7.22 | 6.02 | 7.01 |

The monomeric sugar recoveries (Table 1B), particularly of xylose, were quite poor at the lower EtOH concentrations. At low EtOH concentration, the acidic conditions, produced at high temperatures by hydrolysis of the acetyl groups of the hemicellulose, hydrolyze the hemicellulose. The solubilized xylose and some glucose is lost in the filtration and washes that follow the pretreatment. At higher EtOH concentrations there is less partial hydrolysis of the cellulose, hemicellulose and lignin which lowers the saccharification yield. The behavior at the low and high ethanol concentrations together produce low overall yields of monomeric glucose and xylose.

Example 2

Effect of Alkaline Organic Solvent Solution Pretreatment on Lignin Extraction The purpose of this Example was to examine the effect of raising the pH on organic solvent solution pretreatment at different EtOH in $H_2O$ ratios on carbohydrate retention and lignin extraction and on monomeric sugar during subsequent enzymatic saccharification. Given that autohydrolysis lowers the pH, hydrolyzes xylan, and promotes the loss of xylose, the pH of the pretreatment was elevated by the addition of NaOH. The effect of higher pH on xylose recovery is demonstrated below. Sugar cane bagasse (0.25 g, 95.78% dry matter) was suspended in 1.75 mL of a solvent containing EtOH (20-80% in water) and 8% NaOH (w/w biomass) plus 1 mg anthraquinone (AQ, a catalyst for lignin fragmentation). The initial pH of this solution was ~13.7. As described in Example 1, the suspensions were loaded into type 316 stainless steel tubing, capped, treated at 168° C. for 140 min and cooled in room-temperature water. The samples were removed from the pressure vessels, filtered, washed, air-dried and analyzed all as described above in Example 1. The glucan, xylan, arabinan contents and change in lignin content following pretreatment are shown in Table 2A.

Subsequent enzymatic saccharification was carried out as described in Example 1 except that the Spezyme:Multifect: Novozymes 188 ratio was 12:6:1.2 mg/g dry solids in the presence of 1% Tween 20 (w/v). Table 2B shows the monomeric sugar yields after 96 h of enzymatic saccharification of biomass previously pretreated at the different EtOH concentrations.

TABLE 2A

Glucan, xylan and arabinan yields following pretreatment according to Example 2

| Pretreatment % EtOH in water | % Glucan recovery in residue | % Xylan recovery in residue | % Arabinan recovery in residue | Al lignin content % change |
|---|---|---|---|---|
| 20 | 77.5% | 74.6% | 51.3% | −48 |
| 45 | 84.0% | 85.1% | 68.0% | −64 |
| 60 | 83.6% | 85.5% | 76.0% | −63 |
| 70 | 81.3% | 84.2% | 75.8% | −65 |
| 80 | 80.0% | 84.2% | 86.6% | −50 |

TABLE 2B

Monomeric glucose and xylose yields following enzymatic saccharification for 96 h, pretreated as described in Example 2

| % EtOH in $H_2O$ | Glucose monomer saccharification only (% theoretical yield) | Xylan monomer saccharification only (% theoretical yield) | Glucose monomer overall yield (% theoretical yield) | Xylose monomer overall yield (% theoretical yield) |
|---|---|---|---|---|
| 20 | 57.72 | 68.56 | 44.7 | 51.2 |
| 45 | 58.19 | 73.08 | 48.9 | 62.2 |
| 60 | 49.51 | 64.56 | 41.4 | 55.2 |
| 70 | 24.48 | 39.06 | 19.9 | 32.9 |
| 80 | 0.63 | 1.33 | 0.5 | 1.1 |

As can be seen in Tables 2A and 2B, the alkaline conditions of this experiment substantially increased the retention of xylan in the pretreatment compared to the autohydrolysis experiments of Example 1. This effect was most pronounced at low EtOH concentrations. The NaOH prevented the solution from becoming acidic (final pH ~10.7) and therefore protected the hemicellulose from acid-catalyzed hydrolysis. In addition, significantly more lignin was extracted, presumably through base catalyzed fractionation of the lignin. The overall monomeric sugar yields following saccharification were substantially higher than those observed in Example 1. The higher sugar recovery and the greater lignin extraction in the pretreatment, increased the yields of the subsequent enzymatic saccharification. The xylose and glucose saccharification yields peaked at ~45% EtOH as a consequence of two opposing processes, i.e., the increasing extraction of lignin at higher EtOH which tends to increase the sugar yields, and the decreasing partial hydrolysis of hemicellulose and of lignin as the EtOH concentration is further increased. It is likely that the formation of quinone methides, which could repolymerize or react with sugars, and "peeling' and alkaline scission reactions of polysaccharide all together contribute to limit the overall sugar yields.

Example 3

Pretreatment of Biomass Using Elemental Sulfur During Lignin Extraction

The purpose of the Example was to study the effect of elemental sulfur in biomass pretreatment. Consequently, elemental sulfur was either added or not to the biomass at a concentration equal to 1% or 2% of the weight of the biomass. Pretreatment was performed as in Example 1 except that sugar cane bagasse (0.375 g, 95.78% dry matter) with and without sulfur was suspended in 1.125 mL of solvent (70% EtOH in $H_2O$ (v/v)) containing 14% MA (w/w biomass). The suspensions were loaded into type 316 stainless steel pressure vessels (3/16 inches ID, ¼ inches OD, 4 inches long), capped and treated as described above in Example 1, except that solids loading was higher and the samples were heated to 187° C. for 1 h. After rapid cooling of the pressure vessels to room temperature, the contents were filtered and washed with 70% EtOH in $H_2O$ (v/v) and left to air dry. The filtrate obtained after the pretreatment at 2% sulfur was diluted 1:5000 with 70% EtOH in $H_2O$ (v/v) and the UV spectrum was recorded. As shown in FIG. 1, there is a substantial enhancement in the UV absorbance in the presence of 14% MA (w/w biomass) plus 2% sulfur (w/w biomass) as compared to the 14% MA (w/w biomass) alone in 70% EtOH in $H_2O$ (v/v). The increased extraction of lignin in the presence of sulfur is consistent with the decreased content of lignin in the solids following pretreatment and the enhanced monomeric sugar yield following enzymatic saccharification (Table 3).

The subsequent enzymatic saccharification was performed for 96 h as described in Example 1 except that the Spezyme: Multifect:Novozymes 188 ratio was 6.68:3.34:1.67 mg/g dry solids in the presence and absence of 1% Tween 20 (w/v) or 0.5% PEG 2000 (w/w biomass) at a solids loading of 14% (w/w). The sample not pretreated with 1% sulfur was saccharified in either the presence or absence of 1% Tween 20 (w/v) while the sample pretreated with 1% sulfur was saccharified in the presence and absence of 0.5% PEG 2000 (w/w biomass). Parallel experiments (not shown) have indicated that 1% Tween 20 (w/v) and 0.5% PEG 2000 (w/w biomass) give virtually the same degree of enhancement to the enzymatic saccharification. Pretreatment yields and enzymatic saccharification yields in the presence and absence of 1% Tween 20 (v/v) at 96 h following pretreatment in 70% EtOH plus 14% MA and in the presence and absence of 0.5% PEG 2000 (w/w biomass) following pretreatment in 70% EtOH plus 14% MA plus 1% S (w/w biomass) are shown in Table 3.

Example 4

Effect of Addition of Ammonia to Organic Solvent Solution Pretreatment Containing Methylamine and Elemental Sulfur Pretreatment was performed as in Example 3 except that the bagasse contained 1% elemental sulfur (w/w biomass) and was suspended in 70% EtOH in $H_2O$ (v/v) plus either 14% MA (methylamine), 7% $NH_3$+7% MA, 10% $NH_3$+4% MA, or 14% $NH_3$ (all w/w biomass). The samples were heated at 187° C. for 1 h in pressure vessels and then rapidly cooled to room temperature in water bath. The residue was filtered, washed and dried as previously described. Enzymatic saccharification was performed as in Example 3, but in the presence and absence of 0.5% PEG 2000 (w/w biomass).

TABLE 4

The yield of monomeric sugars following treatment described in Example 4

| Sample 70% EtOH in $H_2O$ (v/v) + 1% S+ | % Glucan recovery in solids | % Xylan recovery in solids | Monomeric glucose (% of theoretical yield) without PEG | Monomeric xylose (% of theoretical yield) without PEG | Monomeric glucose (% of theoretical yield) with PEG | Monomeric xylose (% of theoretical yield) with PEG |
|---|---|---|---|---|---|---|
| 14% MA | 96.8 | 102.3 | 83.3 | 74.6 | 85.8 | 75.8 |
| 7% $NH_3$ + 7% MA | 90.80 | 96.98 | 79.5 | 68.2 | 82.9 | 71.1 |
| 10% $NH_3$ + 4% MA | 91.61 | 97.35 | 76.2 | 66.4 | 80.8 | 68.7 |
| 14% $NH_3$ | 95.24 | 100.41 | 66.71 | 59.5 | 74.3 | 63.9 |

As indicated in Table 4, replacement of methylamine with ammonia does not have an impact on the glucan and xylan recovery upon pretreatment. The saccharification yields for both monomeric glucose and xylose, however, decrease progressively the more extensive the replacement of methylamine with ammonia. The differences between the saccharification runs with and without PEG 2000 are for the most part only a few percent. An economic analysis of the overall process is required to determine whether there is a savings in the cost of sugar production upon either the replacement of methylamine with ammonia in the pretreatment, despite the loss in yield, or upon addition of PEG 2000 in the saccharification, despite the cost of the additive.

TABLE 3

Yields of glucan and xylan following pretreatment according to Example 3

| Sample | % Glucan recovery in solids | % Xylan recovery in solids | Al lignin (% content change) | Monomeric glucose (% of theoretical yield) | Monomeric xylose (% of theoretical yield) |
|---|---|---|---|---|---|
| 70% EtOH, 14% MA | 99.22 | 102.95 | −51 | 71.8 | 59.1 |
| 70% EtOH, 14% MA + 1% Tween 20 (v/v) | 99.22 | 102.95 | −51 | 78.0 | 68.1 |
| 70% EtOH, 14% MA + 1% S | 97.58 | 100.42 | −77 | 86.0 | 82.8 |
| 70% EtOH, 14% MA + 1% S + 0.5% PEG 2000 | 97.58 | 100.42 | −77 | 88.1 | 84.2 |

The addition to the biomass of 1% (w/w biomass) of elemental sulfur produces a substantial increase in the enzymatic saccharification yield of glucose and xylose, both in the presence and in the absence of surfactant. The presence of the sulfur, in addition to increasing the sugar yields, modifies the residual lignin to the point where the addition of PEG 2000 produces only a very small increase in the enzymatic sugar yield.

Example 5

Organic Solvent Solution Pretreatment of Corn Cob, Switchgrass and Sugar Cane Bagasse Using Methylamine and Elemental Sulfur The organic solvent solution plus methylamine plus elemental sulfur pretreatment was tested on three different biomass using conditions similar to those of Example 3 except that the biomass was mixed with 1% elemental sulfur (w/w biomass) in all cases and suspended in 70% EtOH in $H_2O$ containing 14% methylamine (w/w biomass). Switchgrass and sugar cane bagasse were heated at 183° C. for 1 h. Corn cob was heated at 187° C. for 1 h. The samples were washed with 70% EtOH in $H_2O$ (v/v) and air-dried as in Example 3 and then saccharified as described in Example 3 except that the saccharifications were performed in the presence and absence of PEG 2000 (0.5 wt % of biomass). The monomeric sugar yields are shown in Table 5.

TABLE 5

The yield of monomeric sugars following treatment described in Example 5

| Sample | Glucose monomer, sacch. only (% of theoretical yield) without PEG | Glucose monomer, sacch. only (% of theoretical yield) with PEG | Xylose monomer, sacch. only (% of theoretical yield) without PEG | Xylose monomer, sacch. only (% of theoretical yield) with PEG |
|---|---|---|---|---|
| Corn cob, 187° C. | 81.99 | 82.67 | 39.06 | 47.65 |
| Switchgrass, 183° C. | 82.06 | 82.95 | 43.58 | 59.26 |
| Bagasse, 183° C. | 79.84 | 80.5 | 68.51 | 70.92 |

The monomeric glucose yields differ very little between the different feedstocks (e.g., corn, switchgrass and bagasses) and there is little effect of the addition of PEG 2000. The overall oligomer plus monomer xylose yields were similar for the three feedstocks, but the ratio of monomer to oligomer differed appreciably, with bagasse giving the highest monomer/oligomer ratio and corn cob the least. The extent of monomer formation increased somewhat for cob and switchgrass with the addition of PEG, but very little for bagasse. It is likely that structural differences between the xylose oligomers, solubilized in the different feedstocks, account for the differences in their enzymatic conversion to monomer and not the efficacy of the pretreatment.

These results demonstrate the range of applicability of the developed pretreatment to feedstocks that differ appreciably in their lignin composition-corn cob ~14% of DM and switchgrass and bagasse each ~25% of DM.

Example 6

Comparison of Enzymatic Saccharification of Corn Cob, Pretreated Using Organic Solvent Solution in the Presence of Methylamine and Elemental Sulfur, to Cob Pretreated with Dilute Ammonia and to Untreated Cob Two batches of 134 g (8.4% moisture content) hammermilled corn cob, one with 0.5% and the other with 1% elemental sulfur (w/w biomass), were each suspended in 280 mL EtOH, 66.7 mL water, 53.3 mL methylamine solution (47.4 g) and heated to 195° C. for 1 h at temperature with mechanical stirring in a 1 L pressure vessel. Each batch was then washed with 70% EtOH in $H_2O$ (v/v) 3 times. The material was air dried and the two batches were pooled.

Dilute Ammonia Pretreatment:

To 713 g (5.8% moisture content) of hammermilled corn cob loaded into a 5 L reactor, 138.9 g of $NH_4OH$ solution (29 wt % $NH_3$) and 491.1 g additional water were added to give a 50% solids loading. The reactor was heated to 140° C. for 20 min at temperature. The $NH_3$ was then flashed off while the reactor cooled and was then further removed by vacuum. The contents of the reactor were removed and used for saccharification.

Untreated Biomass:

Untreated (8.4% moisture content) hammermilled corn cob was used as a control for this saccharification study.

Glucan and Xylan contents were determined by using the NREL procedure (see Example 1). Analysis of hydrolyzed sugars was done by HPLC as described above with the exception that the column temp was 65° C. instead of 60° C. Saccharification of this material was done in a 1 L glass Erlenmeyer flask (Chemglass, Vineland, N.J.) on a rotary shaker set to 200 rpm and 48° C. In the comparative saccharifications, 75 mmol sodium citrate buffer at average pH of 5.4-5.6 was used to control the pH. In addition, 5 ppm each of penicillin and virginiamycin antibiotics were added to inhibit bacterial growth and 0.5% PEG 2000 (wt % of solids) was added to decrease enzyme adsorption to lignin. The solids were loaded based on their carbohydrate content, which was 18.3 wt % carbohydrate ((glucan+xylan)/(glucan+xylan+mass of liquid added to biomass)). This corresponded to a solids loading of 20.8%, 25.2% and 25.6% for the organic solvent solution, dilute ammonia and untreated material, respectively. The enzymes used were described in Example 1. The protein weight ratio of Spezyme:Novozyme188 was 4:1 and the loading of total Spezyme/Novozyme 188 protein was 37.5, 25 and 10 mg protein/g of glucan for the high, medium and low enzyme loadings, respectively. Multifect was loaded at 15, 10 and 4 mg/g of xylan for the high, medium and low enzyme loadings, respectively. The buffer, additional water, enzymes, surfactant and antibiotics were mixed together in a 1 L flask and then the first 60% of the solids were added. The flasks were heated and shaken. After 1 h, the next 20% of solids was added to each flask. The final 20% of solids was added 3 h later. The reactions continued to mix at temperature for a total of 96 h after which point they were removed. A representative sample of each was transferred to a centrifuge vessel, spun in the centrifuge and the liquid fraction was decanted. The solid was resuspended in water, recentrifuged and the liquid separated was again decanted. This was repeated four additional times. The liquid was analyzed for monomer content using the HPLC. The oligomer content was determined by hydrolyzing for 1 h at 121° C. a portion of this wash fraction with sulfuric acid (4% w/v), reanalyzing on the HPLC and the difference with the monomer content was considered to be derived from the oligomers. The monomer and oligomer content produced by enzymatic saccharification is reported as a yield of the initial amount of glucan and/or xylan in the initial solids in the flasks. Results of these experiments are shown in Table 6 below.

TABLE 6

Sugar yield from various types of pretreatments as described in Example 6

| Pretreatment | Enzyme Loading | % glu yield (mono) | % xyl yield (mono) | % glucan converted to glucan oligomers | % xylan converted to xylan oligomers | % glu yield from sacch (mono + oligo) | % xyl yld from sacch (mono + oligo) | % glu + Xyl yield from sacch (mono + oligo) |
|---|---|---|---|---|---|---|---|---|
| EtOH/MA/$S_8$ | High | 80% | 62% | 13% | 39% | 95% | 102% | 98% |
| Dilute $NH_3$ | High | 60% | 42% | 9% | 38% | 71% | 80% | 75% |
| Untreated | High | 24% | 17% | 3% | 4% | 25% | 20% | 23% |
| EtOH/MA/$S_8$ | Medium | 72% | 55% | 10% | 42% | 84% | 97% | 90% |
| Dilute $NH_3$ | Medium | 51% | 36% | 8% | 38% | 60% | 74% | 66% |

TABLE 6-continued

Sugar yield from various types of pretreatments as described in Example 6

| Pretreatment | Enzyme Loading | % glu yield (mono) | % xyl yield (mono) | % glucan converted to glucan oligomers | % xylan converted to xylan oligomers | % glu yield from sacch (mono + oligo) | % xyl yld from sacch (mono + oligo) | % glu + Xyl yield from sacch (mono + oligo) |
|---|---|---|---|---|---|---|---|---|
| Untreated | Medium | 24% | 17% | 3% | 4% | 26% | 20% | 23% |
| EtOH/MA/$S_8$ | Low | 45% | 39% | 5% | 54% | 52% | 94% | 70% |
| Dilute $NH_3$ | Low | 35% | 25% | 7% | 42% | 43% | 68% | 54% |
| Untreated | Low | 19% | 14% | 2% | 2% | 21% | 16% | 19% |

This comparative study demonstrates the efficacy of the organic solvent solution/methylamine/sulfur pretreatment in enhancing the saccharification of pretreated corn cob relative to the dilute ammonia process and to no pretreatment at solids loadings (20.8% w/w for organic solvent solution) in the saccharifier, considerably higher than in the earlier examples (14% w/w). The enzymatic conversion to monomer plus oligomer following the organic solvent solution pretreatment is nearly quantitative at the high enzyme loading. Under all enzyme loadings, the organic solvent solution pretreatment gives the highest conversion to monomer glucose and xylose and to monomer plus oligomer glucose and xylose.

Example 7

Comparison of Performance on Various Feedstocks of Organic Solvent Pretreatment in the Presence of Methylamine and Elemental Sulfur To compare the effect of organic solvent pretreatment with methylamine (MA) and sulfur (S) on five feedstocks, differing in their lignin content, corn cob (AI lignin 14% of dry matter (DM), switchgrass (AI lignin 23.4% of DM), sugar cane bagasse AI (lignin 25% of DM), sugar cane straw (AI lignin 25% of DM) and yellow poplar (AI lignin 20% of DM) were treated in 70% ethanol in water (v/v) containing 10 or 14% MA and elemental S using the conditions detailed in Table 1. The pretreated biomass was then washed, dried and subjected to enzymatic saccharification. Prior to pretreatment, all feedstocks were first milled in a knife mill using a 1 mm sieve. The pretreatments were performed at the indicated solids loadings in 70% EtOH in water (v/v) containing MA and S and heated at the indicated temperatures and duration. The samples were filtered and then washed with 70% EtOH and then allowed to air dry at ambient temperature. The glucan and xylan contents and percent recoveries following the pretreatment are summarized in Table 7. The samples were then saccharified at 48° C. using Spezyme CP:Mutifect Xylanase:Novozyme 188 at a ratio of 6.68:3.34:1.67 mg/g biomass at a solids loading of 14% in 50 mM NaCitrate, pH 4.7 and at the indicated enzyme loadings for the other solids loadings in 50 mM NaCitrate, pH 4.8-4.9. Saccharifications were performed for the indicated times. The monomeric sugar yields were determined by HPLC (BioRad HPX-87H column at 60° C., 0.01 N $H_2SO_4$ mobile phase) as indicated in Example 1 and are based on the sugar content of the pretreated biomass going into the saccharifier. The total sugar concentration (oligomer plus monomer) was determined by taking the supernatant at the end of saccharification and autoclaving for 1 h at 121° C. in 4% $H_2SO_4$ followed by HPLC analysis. The saccharification results are shown in Table 8.

These results show that pretreatment of lignocellulosic biomass with organic solvent, containing methylamine and sulfur, gives treated biomass with a highly conserved and enriched glucan and xylan content across a broad range of feedstocks, differing appreciably in their lignin content. In addition, this pretreatment facilitates the subsequent enzymatic saccharification, giving high yields of soluble sugars for the same collection of feedstocks.

TABLE 7

Glucan and xylan content and recovery following pretreatment, washing and air-drying

| Sample | Glucan content (% of dry matter) | Xylan content (% of dry matter) | % Glucan recovery following pretreatment | % Xylan recovery following pretreatment |
|---|---|---|---|---|
| Corn cob, solids loading 26%, 195° C., 1 h, 70% EtOH (v/v), 14% MA, 0.75% S (wt/wt biomass), washed with 70% EtOH (v/v) and air-dried | 53 | 38 | 97 | 100 |
| Switchgrass, solids loading 18%, 180° C., 1 h, 70% EtOH (v/v), 14% MA, 1% S (wt/wt biomass), washed with 70% EtOH (v/v) and air-dried | 50 | 36 | 93 | 95 |

TABLE 7-continued

Glucan and xylan content and recovery following pretreatment, washing and air-drying

| Sample | Glucan content (% of dry matter) | Xylan content (% of dry matter) | % Glucan recovery following pretreatment | % Xylan recovery following pretreatment |
|---|---|---|---|---|
| Sugar cane bagasse, solids loading 11%, 180° C., 1 h, 70% EtOH (v/v), 14% MA, 1% S (wt/wt biomass), washed with 70% EtOH (v/v) and air-dried | 50 | 33 | 93 | 100 |
| Sugar cane straw, solids loading 26%, 188° C., 1 h, 70% EtOH (v/v), 14% MA, 1% S (wt/wt biomass), washed with 70% EtOH (v/v) and air-dried | 44 | 29 | 87 | 88 |
| Yellow poplar, solids loading 26%, 200° C., 1 h, 70% EtOH (v/v), 14% MA, 1% S (wt/wt biomass), washed with 70% EtOH (v/v) and air-dried | 67 | 26 | 100 | 89 |

TABLE 8

Conversion of glucan and xylan to glucose and xylose, respectively, by enzymatic saccharification

| Sample | Monomeric Glucose (% theoretical yield) | Monomeric Xylose (% theoretical yield) | Glucose monomer + soluble oligomer (% theoretical yield) | Xylose monomer + soluble oligomer (% theoretical yield) |
|---|---|---|---|---|
| Corn cob, solids loading 26%, 190° C., 1 h, 70% EtOH (v/v), 10% MA, 1% S (wt/wt biomass), saccharification 168 h, 14% solids, + 0.5% PEG 2000 (wt/wt biomass) | 92.5 | 54 | | |
| Corn cob, solids loading 26%, 195° C., 1 h, 70% EtOH (v/v), 14% MA, 0.75% S (wt/wt biomass), saccharification 96 h, 18.5% carbohydrate loading, Spe + Novo 188 (37.5 mg/g glucan), Multifect 15 mg/g xylan | 78 | 59 | 92 | 96 |
| Switchgrass, solids loading 26%, 180° C., 1 h, 70% EtOH (v/v), 14% MA, 1% S (wt/wt biomass), saccharification 168 h, 14% solids + 0.5% PEG 2000 (wt/wt biomass) | 92 | 68 | | |
| Switchgrass, solids loading 18%, 180° C., 1 h, 70% EtOH (v/v), 14% MA, 1% S (wt/wt biomass), saccharification 96 h, 15% carbohydrate loading, Spe + Novo 188 (37.5 mg/g glucan), Multifect 15 mg/g xylan | 71 | 49 | 78 | 89 |
| Sugar cane bagasse, solids loading 26%, 180° C., 1 h, 70% EtOH (v/v), 14% MA, 1% S (wt/wt biomass), saccharification 168 h, 14% solids | 89 | 85 | | |
| Sugar cane bagasse, solids loading 11%, 180° C., 1 h, 70% EtOH (v/v), 14% MA, 1% S (wt/wt biomass), saccharification 96 h, 11.5% carbohydrate loading, Spe + Novo 188 (37.5 mg/g glucan), Multifect 15 mg/g xylan | 89 | 53 | 95 | 92 |
| Sugar cane straw, solids loading 26%, 188° C., 1 h, 70% EtOH (v/v), 14% MA, 1% S (wt/wt biomass), saccharification 144 h, 14% solids, + 0.5% PEG 2000 (wt/wt biomass) | 95 | 67 | | |

TABLE 8-continued

Conversion of glucan and xylan to glucose and xylose, respectively, by enzymatic saccharification

| Sample | Monomeric Glucose (% theoretical yield) | Monomeric Xylose (% theoretical yield) | Glucose monomer + soluble oligomer (% theoretical yield) | Xylose monomer + soluble oligomer (% theoretical yield) |
|---|---|---|---|---|
| Yellow poplar, solids loading 26%, 200° C., 1 h, 70% EtOH (v/v), 14% MA, 1% S (wt/wt biomass), saccharification 168 h, 14% solids, + 0.5% PEG 2000 (wt/wt biomass) | 90 | 60 | 100 | 91 |

What is claimed is:

1. A method for producing carbohydrate-enriched biomass comprising:
   (a) providing lignocellulosic biomass comprising lignin;
   (b) suspending the biomass of (a) in an organic solvent solution comprising water and elemental sulfur under alkaline conditions whereby a biomass-solvent suspension is formed;
   (c) heating the biomass-solvent suspension to a temperature of about 100° C. to about 220° C. for about 5 minutes to about 5 hours whereby lignin is fragmented and is dissolved in the suspension; and
   (d) filtering free liquid whereby the dissolved lignin is removed and whereby readily carbohydrate-enriched biomass is produced.

2. The method of claim 1 further comprising:
   (e) washing the biomass produced in step (d) with a solvent solution.

3. The method of claim 2, further comprising:
   (f) washing the biomass produced in step (e) with water to produce readily saccharifiable carbohydrate-enriched biomass.

4. The method of claim 2 further comprising drying the biomass produced in step (e) to produce readily saccharifiable carbohydrate-enriched biomass.

5. The method of claim 2 or 3, further comprising repeating steps (e) and (f) one or more times.

6. The method of claim 1 wherein the heating step of (c) occurs in a sealed pressure vessel.

7. The method of claim 1 wherein the filtering step of (d) occurs under pressure.

8. The method of claim 1 wherein the organic solvent solution further comprises an additional nucleophile selected from the group consisting of $NH_3$, NaOH, one or more alkylamines, sulfide reagents, and combinations thereof.

9. The method of claim 8 wherein the additional nucleophile is one or more alkylamine and said one or more alkylamine is at a concentration of about up to 20% by weight of dry biomass.

10. The method of claim 1 wherein the solvent solution to biomass in step (b) has a weight ratio of about 10 to 1 to 0.5 to 1.

11. The method of claim 1 wherein the heated suspension of step (c) is cooled to room temperature before filtering in step (d).

12. The method of claim 2 further comprising evaporating off the solvent under vacuum of the filtered and washed biomass after step (e).

13. The method of claim 3, 4 or 12, further comprising saccharifying the biomass with an enzyme consortium whereby fermentable sugars are produced.

14. The method of claim 3 further comprising saccharifying the biomass without drying by contacting said biomass with an enzyme consortium after washing in step (f), whereby fermentable sugars are produced.

15. The method of claim 13 or 14, further comprising fermenting the sugars to produce a target product.

16. The method of claim 15 wherein the target product is selected from the group consisting of alcohols, organic acids, amino acids and gases.

17. The method of claim 1 wherein the biomass is selected from the group consisting of switchgrass, waste paper, sludge from paper manufacture, corn fiber, corn cobs, corn husks, corn stover, grasses, wheat, wheat straw, hay, barley, barley straw, rice straw, sugar cane bagasse, sugar cane straw, yellow poplar, sorghum, soy, components obtained from processing of grains, trees, branches, roots, leaves, wood chips, sawdust, shrubs and bushes, vegetables, fruits, flowers, animal manure and combinations thereof.

18. A method of simultaneous fragmentation and selective extraction of lignin from lignocellulosic biomass to produce a substantially lignin-free biomass comprising:
   (a) providing:
      1) an amount of lignocellulosic biomass:
      2) elemental sulfur and a multi-component solvent solution comprising from about 40% to about 70% ethanol in water (v/v) and one or more alkylamine(s);
   (b) contacting said biomass with the elemental sulfur and the multi-component solvent solution of (a) whereby a biomass-solvent mixture is formed;
   (c) placing the mixture of (b) in a pressure vessel whereby the mixture is heated from about 100° C. to about 220° C. for about 5 minutes to about 5 hours whereby lignin is fragmented and dissolved in the solvent;
   (d) removing the dissolved lignin of (c) by filtration; and
   (e) washing the residual biomass with a organic solvent, whereby substantially lignin-free biomass is produced.

19. The method of claim 18 wherein the substantially lignin-free biomass is from about 60% to about 100% original weight of the biomass.

20. The method of any one of claim 1 or 18, wherein the organic solvent solution further comprises one or additional component selected from the group consisting of alkali or alkaline earth hydroxides or carbonates, ammonia, thiols, polysulfides, hydropolysulfides and hydrosulfides, sulfides and combinations thereof.

21. The method of claim 1 or 18 wherein the solvent solution, and any unreacted elemental sulfur or other unreacted components are recyclable.

22. The method of claim 1 or 18 wherein said organic solvent solution comprises a solvent selected from the group consisting of alcohols, diols and aprotic solvents 23. The method of claim 22 wherein the organic solvent solution comprises a solvent selected from the group consisting of methanol, ethanol, propanol, butanol, pentanol and hexanol, isomers thereof, and diols thereof.

24. The method of claim 1 or 18 wherein the lignocellulosic biomass of step (a) has a carbohydrate content that is highly conserved through steps (a) through (d).

25. The method of claim 7 or 18 wherein the one or more alkylamines is selected from the group consisting of $R-NH_2$, $R_2-NH$, $R_3N$, $(H_2N-R-NH_2)$, $(H_2N-R(NH_2)_2)$, $(HO-R-NH_2)$, $((HO)_2-R-NH_2)$, $(HO-R-(NH_2)_2)$, $(HS-R-NH_2)$, $((HS)_2-R-NH_2)$, $(HS-R-(NH_2)_2)$ and $(H_2N-R(OH)(SH)$ and combinations thereof, wherein R is independently a monovalent, divalent or trivalent 1-6 carbon alkane, alkene or alkyne, linear, cyclic or branched.

26. The method of claim 25 wherein R is independently methyl, ethyl, propyl or butyl.

27. The method of claim 25 wherein the alkylamine is methylamine.

28. The method of claims 1 and 18 wherein the temperature of step (c) is from about 165° C. to about 195° C.

* * * * *